United States Patent [19]

Horn et al.

[11] Patent Number: 4,950,654

[45] Date of Patent: Aug. 21, 1990

[54] HYDROPHILIC THEOPHYLLINE POWDER FORMULATION AND ITS PREPARATION

[75] Inventors: Dieter Horn, Heidelberg; Goetz Krueger, Aachen; Reinhard Spengler, Ludwigshafen, all of Fed. Rep. of Germany

[73] Assignee: Basf Aktiengesellschaft, Ludwigshafen, Fed. Rep. of Germany

[21] Appl. No.: 388,805

[22] Filed: Aug. 3, 1989

[30] Foreign Application Priority Data

Aug. 12, 1988 [DE] Fed. Rep. of Germany ....... 3827362

[51] Int. Cl.$^5$ .................... A61K 31/52; A61K 31/715
[52] U.S. Cl. ..................................... 514/53; 514/263; 544/267; 260/403
[58] Field of Search ................. 514/53, 263; 544/267; 260/403

[56] References Cited

U.S. PATENT DOCUMENTS

| | | |
|---|---|---|
| 4,117,132 | 6/1976 | Seebach . |
| 4,141,986 | 2/1979 | Cassidy et al. ................. 514/210 |
| 4,632,822 | 12/1986 | Peters et al. .................. 514/826 |
| 4,707,481 | 11/1987 | Amschler et al. ............... 514/247 |
| 4,732,901 | 3/1988 | Buckle ........................ 514/277 |
| 4,755,525 | 7/1988 | Markwell et al. ............... 514/394 |

FOREIGN PATENT DOCUMENTS 932874 3/1962 United Kingdom .

OTHER PUBLICATIONS

Chemical Abstracts, Band 109, Nr. 22, Nov. 28, 1988, Seite 456, Zusammenfassung Nr. 197189s, Columbus, OH, U.S. & JP-A-No. 62 286 921, Taisho Pharmaceutical Co., Ltd. 12-12-87.
Chemical & Pharmaceutical Bulletin, Band 35, No. 10, Oct. 1987, Seiten 4271–4276, Pharmaceutical Society of Japan, Tokyo, Japan; Nishihata et al.; "Use of Hydrogenated Soya Phospholipids as a Diluent".
Cur. Ther. Res., vol. 21, No. 2, 233, 1977.

*Primary Examiner*—Robert A. Wax
*Assistant Examiner*—Pamela S. Webber
*Attorney, Agent, or Firm*—Oblon, Spivak, McClelland, Maier & Neustadt

[57] ABSTRACT

A hydrophilic theophylline powder formulation consisting of
(a) from 5 to 15% by weight of theophylline,
(b) from 15 to 30% by weight of lechithin,
(c) from 45 to 80% by weight of sugar,
(d) from 0 to 5% by weight of a flow agent and
(e) from 0 to 30% by weight of further additives, and a process for its preparation.

5 Claims, No Drawings

HYDROPHILIC THEOPHYLLINE POWDER FORMULATION AND ITS PREPARATION

The present invention relates to a process for the preparation of a solid oral theophylline formulation which disperses in water prior to application, is distinguished by fast active compound liberation kinetics and substantially avoids the bitter theophylline taste.

Theophylline and its water-soluble salts with organic bases are powerful bronchospasmolytics and, because of the vasodilatory action, are also widely used in cardiovascular therapy.

A well-known problem in the oral administration of pure theophylline involves fluctuating absorption and bioavailability due to the low water solubility of the active compound (about 0.5% at acidic and neutral pH). This fact is all the more important when the low therapeutic index of the substance is taken into account. It is for this reason that efforts have been made to overcome this problem by using special theophylline derivatives or by means of suitable formulations. Various approaches have been adopted:

The salts of theophylline with strong organic bases (ethylenediamine, piperazine, arginine and lysine derivatives, choline, etc.) are generally very watersoluble, but such aqueous solutions can only be usefully employed as injection solutions; in the case of oral administration, the active compound is liberated and precipitated in the acidic gastric medium, giving rise to the known problems of bioavailability. Furthermore, these strongly alkaline derivatives of theophylline may cause irritation of the mucous membrane.

Another solution entails combining theophylline with organic complexing agents or solubilizers (for example 7-oxypropylxanthine derivatives, o-carbamoylphenoxyacetic acid, benzyl alcohol, etc.; cf. for example German Laid-Open Application DOS No. 2,434,335; Helwig, Moderne Arzneimittel, Wissenschaftliche Verlagsgesellschaft Stuttgart, 5th Edition, 1980; D.S. Sitar, J.H. Nadeau and J.R. Ruedy, Cur. Ther. Res. 21 (1977), 233) However, many of these preparations have the disadvantage that the auxiliaries used must also be regarded as active compounds, so that these are in the strict sense combination preparations in which the actual active compound (theophylline) frequently also plays only a minor role in terms of amount.

Moreover, there are commercial preparations containing aqueous/alcoholic theophylline solutions, but, because of their alcohol content, they are unacceptable and are unsuitable for the treatment of young children and infants.

Another possibility is chemical modification of the theophylline. Substitution at the 7-position in the theophylline molecule may lead to very water-soluble and virtually neutral derivatives (for example hydroxyethyltheophylline, hydroxypropyltheophylline and dihydroxypropyltheophylline). However, these derivatives have less activity than theophylline and are also less effective in stimulation of the central nervous system (Helwig. loc. cit.).

It is an object of the present invention to provide a theophylline formulation which overcomes these disadvantages.

We have found that this object is achieved by a hydrophilic theophylline powder formulation consisting of (a) from 5 to 15, preferably from 8 to 12, % by weight of theophylline,
(b) from 15 to 30, preferably from 20 to 25, % by weight of lecithin,
(c) from 45 to 80, preferably from 55 to 70, % by weight of a sugar,
(d) from 0 to 5, preferably from 1 to 3, % by weight of a flow agent and
(e) from 0 to 30, preferably from 0.1 to 5, % by weight of further additives, and by a process for its preparation, wherein the sugar is dissolved in an aqueous theophylline solution at from 70° to 100° C., preferably from 80° to 85° C., the lecithin and, if required, a colorant, a flavoring agent, a stabilizer and/or further additives are then dispersed and, where relevant, dissolved in the solution, the hot solution is spray-dried dried, the powder is screened and if required mixed with a flow agent and, if required, the ready-prepared mixture is agglomerated.

Sucrose is the preferred sugar, but in principle any sugar is suitable.

Porous silica gel is preferred as the flow agent or flow improver; but it is also possible to use other substances, for example starch, maltodextrin or polyvinylpyrrolidone.

Examples of suitable further additives are food colors, flavoring agents, antioxidants, for example a-tocopherol or ascorbyl palmitate, and extenders, and as such particularly sugar.

A particularly preferred embodiment of the invention comprises embedding theophylline in a hydrophilic matrix by spraying, the said matrix essentially consisting of sugar and refined (purified) soya lecithin. The ready-prepared product is a dry powder having a theophylline content of about 10%.

This dry powder can readily be converted into dispersions having active compound contents of up to 20 g/l by stirring into water or other aqueous liquids, such as milk, juices, tea, etc. Although they have concentrations well above the saturation limit, these dispersions surprisingly remain free of deposited active compound over sufficiently long periods (more than 30 minutes).

Trials with test subjects using subtherapeutic doses have shown that the theophylline in the formulations according to the invention has invasion kinetics similar to that of the rapidly released forms described in the literature but without having their disadvantages described at the outset. It is particularly surprising that the notoriously penetrant bitter taste of the theophylline, which is associated with all preparations known to date, has substantially vanished in the novel formulation, even without flavor improvers. This is a very substantial advantage. Various flavors can be obtained by admixing small amounts of a flavoring agent.

Furthermore the mixture is alcohol-free and therefore also suitable for young children.

The combination of these features gives a property profile which has not been realised in this form to date.

The absorption of the active ingredient was investigated in the following manner:

1,073 mg of dry powder, corresponding to 100 mg of theophylline, were administered orally to each of 7 healthy test subjects. The resulting plasma levels were analyzed; the kinetics were determined.

To ensure that the powder remains in suspension when stirred into aqueous liquids, it may be advantageous to agglomerate (compact) it. This can be done, for example, by allowing the powder to pass between two rollers. This gives a thin shell, ie. a very readily crumbling roll sheet which gives an agglomerated (compacted) powder on screening. Another possible method for agglomeration is, for example, to spray a very small amount of water onto the moving powder (for example a fluidized bed).

EXAMPLE 1

405 g of sucrose were added to a solution of 90 g of theophylline in 3,000 g of water at 80°-85° C., while stirring. After dissolution was complete, 405 g of ®Megglezitin (soya lecithin formulation from Meggle, Wasserburg am Inn) were introduced a little at a time and dispersed using an efficient homogenizer (Ultraturrax). One % by weight, based on lecithin, of a-tocopherol was likewise homogenized in the mixture at this point.

During the entire process, the temperature was kept at 80°-85° C. The hot suspension was then spray-dried, the dry powder was passed through a sieve having a mesh size of 710 lm, and 18 g of ®Aerosil 200 from Degussa were added to improve the flow properties.

The ready-prepared product was a pale, free-flowing powder having the following composition:
9.8% of theophylline,
44.1% of megglezitin,
44.1% of sucrose and
2% of Aerosil 200.

We claim:

1. A hydrophilic theophylline powder formulation, consisting of:
   (a) from 5 to 15% by weight of theophylline,
   (b) from 15 to 30% by weight of lecithin,
   (c) from 45 to 80% by weight of a sugar,
   (d) from 0 to 5% by weight of a flow agent, and
   (e) from 0 to 30% by weight of at least one additive selected from the group consisting food colors, flavoring agents, antioxidants and extenders.

2. The powder formulation of claim 1, wherein said flow agent is a member selected from the group consisting of silica gel, starch, maltodextrin and polyvinylpyrrolidone.

3. A process for the preparation of a hydrophilic theophylline powder formulation as claimed in claim 1, comprising:
   (a) dissolving sugar in an aqueous theophylline solution at a temperature from 70°-100° C. and further dissolving or suspending lecithin and at least one additive selected from the group consisting of a colorant, a flavoring agent, a stabilizer and an extender in the aqueous solution;
   (b) spray-drying the heated solution; and
   (c) screening the dry powder obtained.

4. The process of claim 3, wherein said screened dry powder is mixed with a flow agent.

5. The process of claim 3, wherein the screened dry powder is agglomerated.

* * * * *